US00PP34784P2

(12) United States Plant Patent
Beers

(10) Patent No.: US PP34,784 P2
(45) Date of Patent: Nov. 29, 2022

(54) ***GERBERA* PLANT NAMED 'GLOLIP21AA'**

(50) Latin Name: *Gerbera hybrida*
Varietal Denomination: GLOLIP21AA

(71) Applicant: HilverdaFlorist B.V., De Kwakel (NL)

(72) Inventor: Martin Beers, Hoofddorp (NL)

(73) Assignee: HilverdaFlorist B.V., De Kwakel (NL)

( * ) Notice: Subject to any disclaimer, the term of this patent is extended or adjusted under 35 U.S.C. 154(b) by 0 days.

(21) Appl. No.: 17/747,718

(22) Filed: May 18, 2022

(51) Int. Cl.
*A01H 5/02* (2018.01)
*A01H 6/14* (2018.01)

(52) U.S. Cl.
USPC ..... Plt./357

(58) Field of Classification Search
USPC ..... Plt./263.1 and, 357
See application file for complete search history.

*Primary Examiner* — Karen M Redden
(74) *Attorney, Agent, or Firm* — C. Anne Whealy

(57) ABSTRACT

A new and distinct cultivar of *Gerbera* plant named 'GLOLIP21AA', characterized by its compact, broadly upright and uniformly mounding plant habit; moderately vigorous growth habit; dense and bushy appearance; numerous inflorescences with pink-colored ray florets; upright and moderately strong peduncles; good garden performance and relative tolerance to low temperatures.

1 Drawing Sheet

Botanical designation: *Gerbera hybrida.*
Cultivar denomination: 'GLOLIP21AA'.

BACKGROUND OF THE INVENTION

The present invention relates to a new and distinct cultivar of *Gerbera* plant, botanically known as *Gerbera hybrida* and hereinafter referred to by the cultivar name 'GLOLIP21AA'.

The new *Gerbera* plant is a product of a planned breeding program conducted by the Inventor in De Kwakel, The Netherlands. The objective of the breeding program is to create new compact garden *Gerbera* plants with numerous attractive inflorescences, resistant to cold temperatures and good garden performance.

The new *Gerbera* plant originated from a cross-pollination during the spring of 2015 of a proprietary selection of *Gerbera hybrida* identified as code number 47180, not patented, as the female, or seed, parent with a proprietary selection of *Gerbera hybrida* identified as code number 47275, not patented, as the male, or pollen, parent. The new *Gerbera* plant was discovered and selected as a single flowering plant from within the progeny of the stated cross-pollination in a controlled greenhouse environment in De Kwakel, The Netherlands during the summer of 2016 in De Kwakel, The Netherlands.

Asexual reproduction of the new *Gerbera* plant by vegetative terminal cuttings and in vitro meristem culture since the autumn of 2016 has shown that the unique features of this new *Gerbera* plant are stable and reproduced true to type in successive generations of asexual reproduction.

SUMMARY OF THE INVENTION

Plants of the new *Gerbera* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'GLOLIP21AA'. These characteristics in combination distinguish 'GLOLIP21AA' as a new and distinct *Gerbera* plant:

1. Compact, broadly upright and uniformly mounding plant habit.
2. Moderately vigorous growth habit.
3. Dense and bushy appearance.
4. Numerous inflorescences with pink-colored ray florets.
5. Upright and moderately strong peduncles.
6. Good garden performance and relative tolerance to low temperatures.

Plants of the new *Gerbera* differ primarily from plants of the female parent selection in the following characteristics:

1. Plants of the new *Gerbera* have larger inflorescences than plants of the female parent selection.
2. Plants of the new *Gerbera* have pink-colored ray florets whereas plants of the female parent selection have white-colored ray florets.

Plants of the new *Gerbera* differ primarily from plants of the male parent selection in the following characteristics:

1. Plants of the new *Gerbera* have shorter and narrower leaves than plants of the male parent selection.
2. Plants of the new *Gerbera* have lighter pink-colored ray florets than plants of the male parent selection.

Plants of the new *Gerbera* can be compared to plants of the *Gerbera hybrida* 'MAJLIP20AA', disclosed in a U.S. Plant patent application Ser. No. 17/747,743 filed concurrently. In side-by-side comparisons, plants of the new *Gerbera* differ from plants of 'MAJLIP20AA' in the following characteristics:

1. Plants of the new *Gerbera* are not as vigorous as plants of 'MAJLIP20AA'.
2. Plants of the new *Gerbera* have larger leaves than plants of 'MAJLIP20AA'.

3. Plants of the new *Gerbera* have larger inflorescences than plants of 'MAJLIP20AA'.

BRIEF DESCRIPTION OF THE PHOTOGRAPH

The accompanying photograph illustrates the overall appearance of the new *Gerbera* plant showing the colors as true as it is reasonably possible to obtain in colored reproductions of this type. Colors in the photograph may differ slightly from the color values cited in the detailed botanical description which accurately describe the colors of the new *Gerbera* plant.

The photograph is a side perspective view of a typical flowering plant of 'GLOLIP21AA' grown in a container.

DETAILED BOTANICAL DESCRIPTION

The aforementioned photograph and following observations and measurements describe plants grown during the winter and early spring in 17-cm containers in a glass-covered greenhouse in De Kwakel, The Netherlands and under cultural practices typical of commercial garden *Gerbera* production. During the production of the plants, day and night temperatures ranged from 12° C. to 15° C. Plants were six months old when the photograph was taken and 20 weeks old when the description was taken. In the following description, color references are made to The Royal Horticultural Society Colour Chart, 2015 Edition, except where general terms of ordinary dictionary significance are used.

Botanical classification: *Gerbera hybrida* 'GLOLIP21AA'.

Parentage:

*Female, or seed, parent*.—Proprietary selection of *Gerbera hybrida* identified as code number 47180, not patented.

*Male, or pollen, parent*.—Proprietary selection of *Gerbera hybrida* identified as code number 47275, not patented.

Propagation:

*Type*.—By cuttings and in vitro meristem culture.

*Time to initiate roots, by cuttings, summer and winter*.—About 3.5 weeks at minimum temperatures of 20° C.

*Time to initiate roots, by tissue culture, summer and winter*.—About 2.5 to 3 weeks at minimum temperatures of 20° C.

*Time to produce a rooted young plant, by cuttings, summer and winter*.—About 3.5 weeks after rooting, at temperatures about 20° C. to 26° C.

*Time to produce a rooted young plant, by tissue culture, summer and winter*.—About five to six weeks at temperatures about 20° C. to 26° C.

*Root description*.—Fibrous; typically white in color, actual color of the roots is dependent on substrate composition, water quality, fertilizer type and formulation, substrate temperature and physiological age of roots.

Plant description:

*Appearance*.—Herbaceous perennial that is typically grown as a container or garden plant; compact, broadly upright and uniformly mounding; roughly flattened globular in shape; numerous leaves arranged in basal rosettes; dense and bushy habit; inflorescences held above the foliar plane on erect and strong basal peduncles; moderately vigorous growth habit and moderate growth rate.

*Plant height, soil level to top of foliar plane*.—About 30.9 cm.

*Plant height, soil level to top of inflorescences*.—About 48.2 cm.

*Plant width or spread*.—About 58.7 cm

Leaf description:

*Arrangement*.—Alternate, basal, simple.

*Length*.—About 24.3 cm.

*Width*.—About 12.3 cm.

*Shape*.—Obovate in overall outline.

*Apex*.—Obtuse.

*Base*.—Hastate and short attenuate.

*Margin*.—Coarsely and irregularly angulate to dentate-angulate.

*Texture and luster, upper surface*.—Moderately pubescent; slightly rugose; slightly to moderately glossy.

*Texture and luster, lower surface*.—Moderately to densely pubescent, slightly rugose; matte.

*Venation pattern*.—Pinnate.

*Color*.—Developing leaves, upper surface: Close to 137A. Developing leaves, lower surface: Close to 147B. Fully expanded leaves, upper surface: Close to NN137B; venation, close to 144C. Fully expanded leaves, lower surface: Close to a blend of 147B and 191B; venation, close to 145A.

*Petioles*.—Length: About 11.7 cm. Diameter: About 4 mm. Texture and luster, upper and lower surfaces: Densely pubescent; slightly glossy. Strength: Moderately strong to strong. Color, upper surface: Close to 152A; proximally, close to 176A. Color, lower surface: Close to 146C; proximally, close to 178A.

Inflorescence description:

*Appearance*.—Composite inflorescence form with narrowly oblanceolate-shaped ray florets; solitary inflorescences borne on upright and moderately strong peduncles and held above the foliar plane; ray and disc florets arranged acropetally on a capitulum; inflorescences face upright.

*Fragrance*.—None detected.

*Flowering season*.—Plants begin flowering about three months after planting; under garden conditions in The Netherlands, plants flower from spring to late autumn; plants can be flowered year-round in the greenhouse.

*Inflorescence longevity*.—Depending on the temperature, inflorescences last about two to four weeks on the plant; inflorescences persistent.

*Quantity of inflorescences*.—Freely flowering habit with about 24 inflorescences developing per plant during the flowering season.

*Inflorescence buds*.—Height: About 1.7 cm. Diameter: About 3.2 cm. Shape: Flattened hemispherical. Texture and luster: Densely pubescent; matte. Color: Close to 138C; immature ray florets, close to 151B and 151C.

*Inflorescence size*.—Diameter: About 9.8 cm. Depth (height): About 3.3 cm. Diameter of disc: About 1.7 cm.

*Receptacles*.—Height: About 4 mm. Diameter: About 1.1 cm. Shape: Flattened globular. Color: Close to 157A.

*Ray florets*.—Quantity and arrangement: About 320 per inflorescence; ray florets arranged in about eight outer whorls and two inner whorls of smaller ray florets. Orientation: Proximally, about 40° from vertical; distally, close to horizontal to slightly downward. Outer whorls of ray florets: Length: About 3.8 cm. Width: About 6 mm. Shape: Narrowly oblanceolate. Apex: Narrowly obtuse to shallowly emarginate. Base: Narrowly cuneate. Margin: Entire; not undulate. Texture and luster, upper surface: Smooth, glabrous; velvety; matte. Texture and luster, lower surface: Smooth, glabrous; slightly velvety; slightly carinate; slightly glossy. Color: When opening, upper surface: Close to 52D; apical margins and apices, close to 150D. When opening, lower surface: Slightly lighter than 150D tinged with close to 56B and 56C. Fully opened, upper surface: Close to 52D; towards the base, close to 55D and at the base, close to 155C; venation, similar to lamina colors; color does not change with subsequent development. Fully opened, lower surface: Close to 150D; towards the base, close to 155C; venation, similar to lamina colors; color does not change with subsequent development. Inner whorls of ray florets: Length: About 2.6 cm. Width: About 1 mm. Shape: Narrowly oblanceolate. Apex: Narrowly obtuse to shallowly emarginate. Base: Narrowly cuneate. Margin: Entire; not undulate. Texture and luster, upper surface: Smooth, glabrous; velvety; matte. Texture and luster, lower surface: Smooth, glabrous; slightly velvety; slightly carinate; slightly glossy. Color: When opening, upper surface: Close to 52D; apical margins and apices, close to 150D. When opening, lower surface: Slightly lighter than 150D tinged with close to 56B and 56C. Fully opened, upper surface: Close to 52D; towards the base, close to 55D and at the base, close to 155C; venation, similar to lamina colors; color does not change with subsequent development. Fully opened, lower surface: Close to 150D; towards the base, close to 155C; venation, similar to lamina colors; color does not change with subsequent development.

*Disc florets*.—Quantity and arrangement: About 200 disc florets at center of the inflorescence arranged in about a six-whorl spiral; disc florets do not fully develop. Length: About 5 mm. Width: About 1 mm. Shape: Tubular with one or two narrow free lobes and one broader free lobe. Apex: Acute and recurved. Base: Fused. Margin, free lobes: Entire; not undulate. Texture, upper and lower surfaces: Smooth, glabrous; slightly velvety; slightly glossy. Color: When opening, inner and outer surfaces: Close to 150C; towards the base, close to 157D.

*Pappus*.—Quantity of hairs per floret: Numerous. Length: About 7 mm. Diameter: Less than 1 mm. Texture and luster: Soft; matte. Color: Close to 183D.

*Phyllaries*.—Quantity and arrangement: About 80 per inflorescence arranged in about three whorls. Length: About 1.7 cm. Width (at base): About 2 mm. Shape: Linear. Apex: Narrowly acute. Base: Cuneate. Margin: Entire. Texture and luster, upper surface: Smooth, glabrous; moderately glossy. Texture and luster, lower surface: Densely pubescent; matte. Color, upper surface: Close to 143B. Color, lower surface: Close to 138C.

*Peduncles*.—Length: About 47.7 cm. Diameter: Proximally, about 7 mm; distally, about 6 mm. Strength: Moderately strong. Angle: About 15° from vertical. Texture and luster: Densely pubescent; slightly glossy. Color: Close to 144B; distal end, close to 147C; proximal end, close to 176A.

*Reproductive organs*.—Androecium: To date, as disc florets do not fully develop, stamen development has not been observed on plants of the new *Gerbera*. Gynoecium (present on ray florets): Quantity per floret: One. Pistil length: About 1 cm. Stigma diameter: About 0.5 mm. Stigma shape: Cleft. Stigma color: Close to 54D. Style length: About 9.5 mm. Style color: Close to N155A. Ovary color: Close to 155A.

*Seeds and fruits*.—To date, seed and fruit production has not been observed on plants of the new *Gerbera*.

Pathogen & pest resistance: To date, resistance to pathogens and pests common to *Gerbera* plants has not been observed on plants of the new *Gerbera* grown under commercial production conditions.

Garden performance: Plants of the new *Gerbera* have been observed to have good garden performance and to tolerate temperatures ranging from about −5° C. to about 35° C. and to be cold hardy to USDA Hardiness Zone 7.

It is claimed:

1. A new and distinct *Gerbera* plant named 'GLOLIP21AA' as illustrated and described.

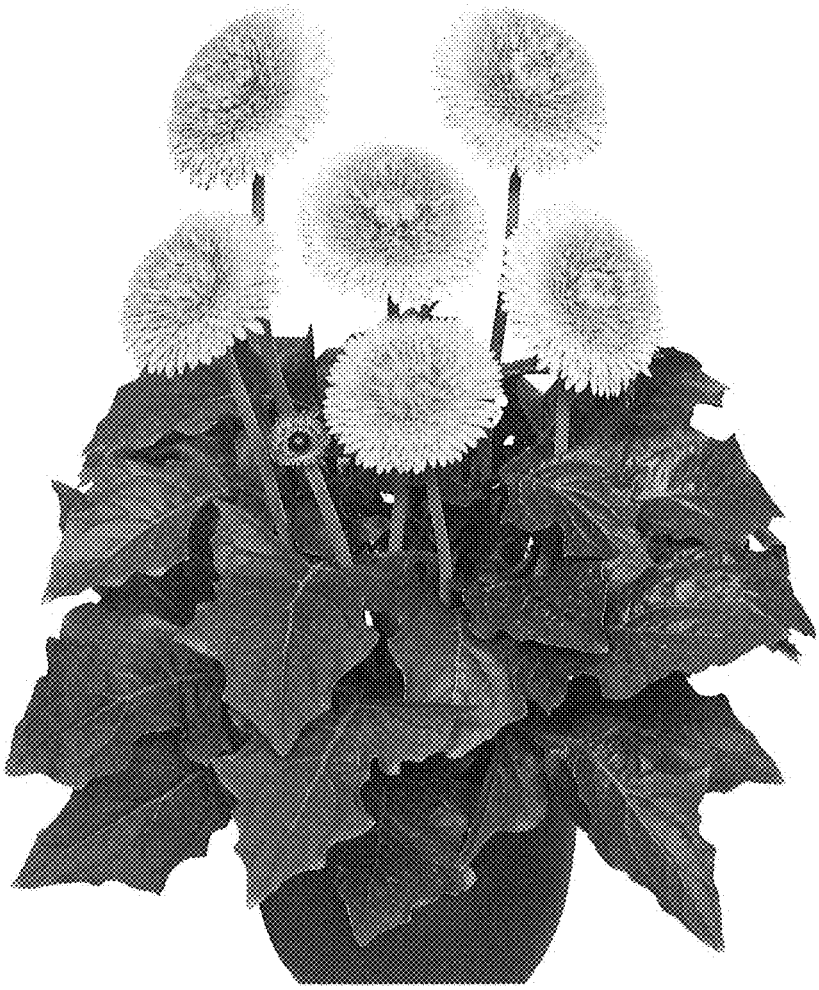

* * * * *